United States Patent [19]

Heilmann et al.

[11] Patent Number: 4,946,962
[45] Date of Patent: Aug. 7, 1990

[54] BIS(THIAZOLINETHIONES)

[75] Inventors: Steven J. Heilmann, N. St. Paul; Larry R. Krepski, White Bear Lake; Jerald K. Rasmussen, Stillwater, all of Minn.; Alan R. Katritzky; Richard D. Tarr, both of Gainesville, Fla.

[73] Assignee: Minnesota Mining and Manufacturing Company, St. Paul, Minn.

[21] Appl. No.: 356,000

[22] Filed: May 23, 1989

Related U.S. Application Data

[62] Division of Ser. No. 843,078, Mar. 24, 1986, abandoned.

[51] Int. Cl.$^5$ .................. C07D 417/04; C07D 417/06; C07D 417/10; C07D 417/12
[52] U.S. Cl. ...................................................... 548/187
[58] Field of Search .......................................... 548/187

[56] References Cited

U.S. PATENT DOCUMENTS

| | | | |
|---|---|---|---|
| 3,068,098 | 12/1962 | Williams | 96/29 |
| 3,072,671 | 1/1963 | Satzinger | 260/306.7 |
| 3,081,170 | 3/1963 | Rauch | 96/109 |
| 3,370,051 | 2/1968 | Sullivan | 260/86.1 |
| 3,433,640 | 3/1969 | Nikkio et al. | 96/107 |
| 4,659,801 | 4/1987 | Katritzky et al. | 528/226 |

FOREIGN PATENT DOCUMENTS 1086657 10/1967 United Kingdom ................. 548/187
2103382A 6/1981 United Kingdom ................. 548/187

OTHER PUBLICATIONS

Chem. Abstracts, 74, 81769k (1971).
Chem. Abstracts, 68, 17421g (1968).
Chem. Abstracts, 74, 70255p (1971).
Chem. Abstracts, 96, 226521q (1982).
Chem. Abstracts, 146144y (1974).
Chem. Abstracts, 17432u (1968).
Chemical Abstracts, V. 98, p. 6960CS (1983), V. 68, p. 3749S (1968).
Daus, JPTOS, 70, pp. 385-387 (1988).
Kulkarni, J. Pharm. Sci. 58,852 1969.
Humphlett, Carbohyd Res. 7 431 1968.
Metzger, Thiazoles and its Derivatives pp. 260-265, 1979.

Primary Examiner—Robert Gerstl
Attorney, Agent, or Firm—Donald M. Sell; Walter N. Kirn; Lorraine R. Sherman

[57] ABSTRACT

Two classes of certain compounds known as bis(-thiazolinethiones), more particularly bis[(3,4-disubstituted)-thiazole-2-thiones], have thiazolinethione heterocycle units linked by alkylene, arylene, or arene groups or by a carbon to carbon single bond. These compounds are useful in the graphic arts because of their reduced volatility, reduced migrating aptitude, and reduced hydrophilicity compared to mono thiazolinethiones.

5 Claims, No Drawings

BIS(THIAZOLINETHIONES)

This application is a division of Ser. No. 843,078 filed Mar. 24, 1986, now abandoned.

FIELD OF THE INVENTION

This invention relates to novel bis(thiazolinethiones) and to a method of preparing them. The compounds are useful in the photographic arts.

BACKGROUND OF THE INVENTION

Photographic elements are often composed of many layers of photosensitive and non-photosensitive materials, with each layer making a unique contribution to achieve a high degree of image quality. In color photography especially, the number of emulsion-applied layers is often considerable, with, in addition to one or more layers being deposited to define the proper level for each of the primary colors, layers being present that are responsible for performing antihalation, filtering, barrier, antistatic, and antiblocking functions. These layers function more or less independently, and it is important that the various components of the layers not migrate into neighboring layers. If migration occurs, the loss of the component not only diminishes overall performance of the function for which it was intended, but the migrated component also can interfere with the function of neighboring layers into which it has migrated. Migration is a serious problem in photography.

The [3H]-thiazole-2-thione heterocycle (I),

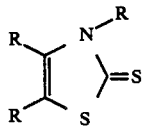

also referred to as a [3H]-thiazoline-2-thione and hereinafter also referred to as thiazolinethione, is known to be extremely useful in the photographic industry. For example, certain low molecular weight thiazolinethione compounds form light-sensitive silver complexes which are useful in coatings for photographic paper (Fr. Demande 2,019,578; Chem. Abstract., 74, 81769k (1971)). Derivatives of (I) have been disclosed to be useful when added to silver halide emulsions to enhance a black tone of an image and to increase the photosensitivity (Brit. 1,086,657; Chem. Abstr., 68, 17421q (1968)). Additional applications of thiazolinethiones in the photographic industry are as desensitizers for direct positive photography. Derivatives of (I), used as silver halide emulsion additives, were disclosed to exhibit more controlled coloring and contrast of photographic materials (Brit. 1,086,613; Chem. Abstr., 68, 17432u (1968); U.S. 3,367,779). Thiazolinethione compounds (I) have also been disclosed to be useful as emulsion additives to reduce fogging during the storage of photographic materials (Fr. Demande 2,019,603; Chem. Abstr., 74, 70255p (1971)) and to prepare photographic emulsions having low visible light sensitivity, high UV sensitivity, and low fog (Jpn. Kokai Tokkyo Koho JP 81,149,031; Chem. Abstr., 96, 226521q (1982)).

U.S. Pat. No. 3,433,640 and UK Patent Application GB 2103382A describe the use of certain thiazoline-2-thiones to improve the photographic characteristics of photographic films. A class of compounds is illustrated by a Markush formula, and specific compounds including compounds

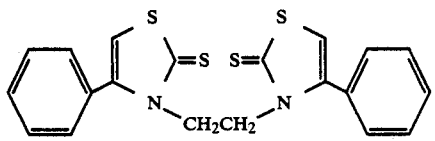

and

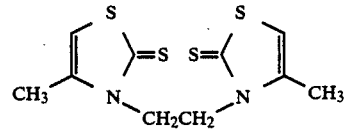

and are disclosed. These patents do not describe any source for these compounds, and do not describe a synthetic method for their preparation. The above-stated patents thus fail to enable one of ordinary skill in the art to make and use these compounds.

Japanese Kokai 73:91,065 (Chemical Abstracts 146,144y, 1974) describes bactericides and fungicides of the formula

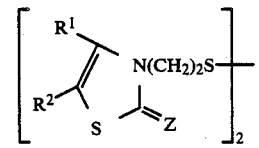

wherein $R^1$ is alkyl or aryl, $R^2$ is hydrogen or alkanoyl, and Z is oxygen, sulfur, alkylimino, arylimino, or aralkylimino.

SUMMARY OF THE INVENTION

Briefly, the present invention provides two classes of bis(thiazolinethiones), also known as bis([3H]-thiazole-2-thiones) or bis[(3,4-disubstituted)-thiazole-2-thiones], which are linked by certain alkylene, arylene or arene groups or a carbon to carbon single bond. In another aspect, this invention relates to methods of preparing the novel compounds.

In this application: "aryl" means the monovalent residue remaining after removal of one hydrogen atom from an aromatic or heteroaromatic compound which can consist of one ring or two fused or catenated rings having 5 to 12 carbon atoms which can include up to 4 heteroatoms selected from S, N, and 0. The carbon atoms can be substituted by up to four halogen atoms or haloalkyl, lower alkyl, lower alkoxy, N,N-di(lower alkyl)amino, nitro, cyano, carboxylic acid ester, carboxylic acid amide and sulfonyl groups;

"arylene" means the divalent residue remaining after removal of two hydrogen atoms from an aromatic or heteroaromatic compound which can consist of one ring or two fused or catenated rings having 5 to 12 carbon atoms which can include up to 4 heteroatoms selected from S, N, and 0. The carbon atoms can be substituted by up to four halogen atoms or haloalkyl, lower alkyl, lower alkoxy, N,N-di(lower alkyl)amino, nitro, cyano, carboxylic acid ester, carboxylic acid amide and sulfonyl groups;

"arene" means the divalent residue remaining after removal of two hydrogen atoms from a hydrocarbon containing both aliphatic and aromatic or heteroaromatic units having up to a total of 20 atoms which can include up to 4 heteroatoms selected from S, N, and O, at least one valence being on the aliphatic portion of the group; the aromatic portion of the group can contain one ring or two fused or catenated rings;

"alkyl" and "alkylene" mean the mono and divalent residues remaining after removal of one and two hydrogen atoms, respectively, of a linear or branched chain saturated hydrocarbon having 1 to 20 carbon atoms; and "lower alkyl", "lower alkylene", or "lower alkoxy" mean a straight or branched chain alkyl, alkylene or alkoxy group having one to four carbon atoms Aromatic and heteroaromatic compounds that provide the aryl and arylene groups useful in the invention include but are not limited to benzene, naphthalene, biphenyl, furan, thiophene, pyrrole, pyridine, pyrazine, pyrimidine, pyridazine, imidazole, pyrazole, oxazole, isoxazole, thiazole, bipyridine, quinoline, isoquinoline, triazole, oxadiazole, thiadiazole, triazine, tetrazole; arene groups are provided by lower alkylene derivatives of the above-mentioned aromatic and heteroaromatic compounds.

DETAILED DESCRIPTION OF THE INVENTION

The present invention relates to bis(thiazolinethiones) having the formulae

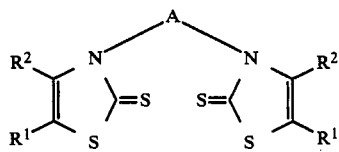  II and

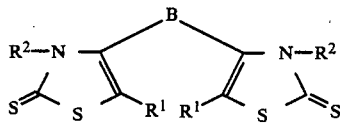  III wherein $R^1$ can be hydrogen, a lower alkyl group having 1 to 4 carbon atoms, or an aryl group having 5 to 12 ring atoms, $R^2$ can be hydrogen, an alkyl group of 1 to 20 carbon atoms, or an aryl group of 5 to 12 ring atoms, A can be a branched or straight chain alkylene group having 2 to 20 carbon atoms, preferably 3 to 20 carbon atoms, more preferably 5 to 20 carbon atoms and most preferably 6 to 20 carbon atoms, that can be interrupted by one or more non-adjacent oxygen or sulfur atoms, or

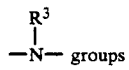 groups wherein $R^3$ is hydrogen or a lower alkyl group, an arylene group having 5 to 12 ring atoms, or an arene group having 6 to 20 atoms, B can be a carbon to carbon single bond, a branched or straight chain alkylene group having 1 to 20 carbon atoms, preferably 3 to 20 carbon atoms, that can be interrupted by one or more non-adjacent oxygen or sulfur atoms, an arylene group having 5 to 12 ring atoms, or an arene group of 6 to 20 atoms, or

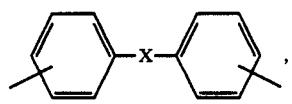

wherein X can be a branched or straight chain alkylene group of 1 to 4 carbon atoms,

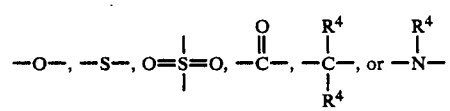

wherein $R^4$ is independently H or a lower alkyl group.

Preferred A groups include alkylene groups having 2 to 20 carbon atoms such as dimethylene, trimethylene, tetramethylene, pentamethylene, hexamethylene, octamethylene, dodecamethylene,

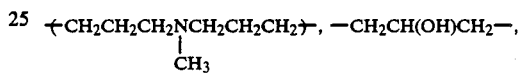

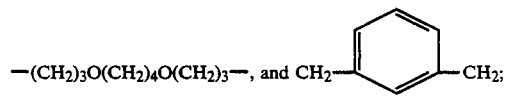

most preferred A groups include alkylene groups having 3 to 20 carbon atoms, arylene groups having 5 to 12 ring atoms, or arene groups having 6 to 20 atoms, because of reduced volatility, reduced migratory aptitude, and reduced hydrophilicity of the resulting compounds.

Preferred B groups include trimethylene, tetramethylene, hexamethylene, octamethylene, para-phenylene; para, para'-biphenylene; para, para'-oxydiphenylene; para, para'-thiodiphenylene; and para, para'-methylenediphenylene,

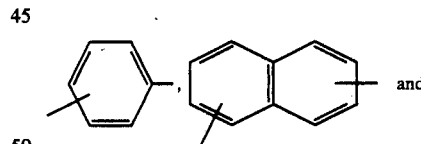 and

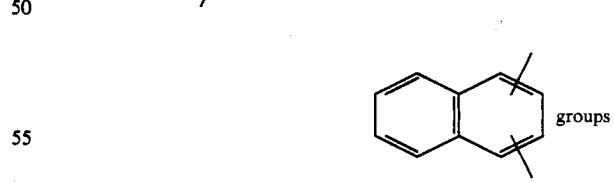 groups because of reduced volatility, reduced migratory aptitude, and reduced hydrophilicity; most preferred B groups, because of ease of synthesis, include arylene groups having 5 to 12 ring atoms.

$R^1$ preferably is hydrogen, methyl, or phenyl; and $R^2$ preferably is methyl, phenyl, p-methoxyphenyl, or m-nitrophenyl.

In the method of the invention bis(thiazolinethione) compounds of Formula II can be prepared according to Reaction Scheme I, below.

Reaction Scheme I $$CS_2 + NH_2-A-NH_2 + MQ \xrightarrow{(1)} A(NHCSSM)_2$$

IV

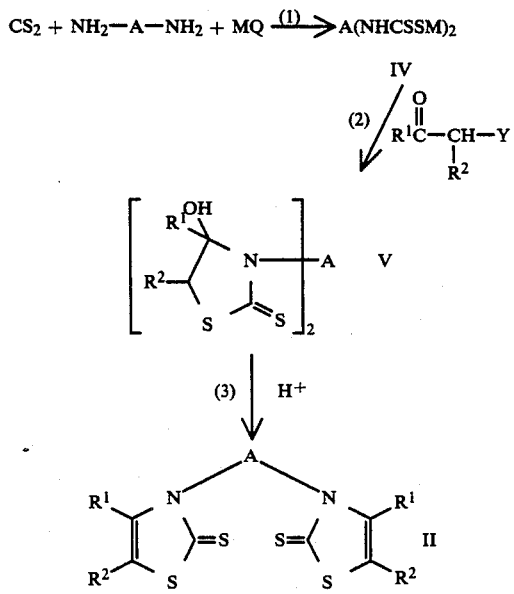

wherein M is an ammonium ion or an alkali metal ion such as $Na^+$ or $K^+$, Y is halogen such as Cl or Br, and Q is a hydroxyl or carboxylate ion such as acetate, propionate, benzoate, and the like, and $R^1$, $R^2$ and A are as defined above In Step (1) carbon disulfide is reacted with a diamine such ask 1,2-ethylenediamine, 1,3-propylenediamine or 1,4-butylenediamine in the presence of a base such as potassium acetate, potassium hydroxide, or sodium hydroxide. to provide a salt of a bis(dithiocarbamate) of Formula IV. This preparation is described in detail for 1,6-hexanediamine and $CS_2$ by M. Bogemann, et al., in "Houben Weyl Methoden der Organischen Chemie", Vol. 9, Georg Thieme Verlag, Stuttgart, Germany, p. 870 (1955).

In Step (2) a salt of a bis(dithiocarbamate) is reacted with an alpha-haloketone such as an alpha-haloacetophenone in a polar solvent such as N,N-dimethylformamide, N,N-dimethylacetamide, dimethylsulfoxide, or ethanol at a temperature in the range of 0° to 50° C. for 2 to 48 hours.

In Step (3) the reaction mixture is treated with 0.1 to 10 equivalents of an aqueous acid of pH 6 or less, such as acetic, hydrochloric, nitric, or sulfuric acid, and the mixture is heated at 50 to 100° C. for 1 to 5 hours. This step effects dehydration of the bis(thiazolidinethione) compound of Formula V to form the bis(thiazolinethione) compound of Formula II.

Steps (1), (2) and (3) are optionally carried out in the same reaction vessel without isolating the salt of the bis(dithiocarbamate).

Bis(thiazolinethione) compounds of Formula III are prepared according to Reaction Scheme II, below.

Reaction Scheme II

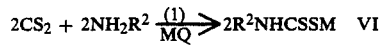

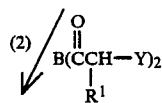

-continued
Reaction Scheme II

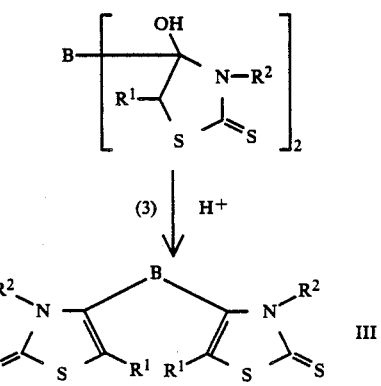

wherein M, Q, $R^1$, $R^2$, B, and Y are as defined above.

In Step (1) of Reaction Scheme II carbon disulfide is reacted with an aliphatic primary amine such as methylamine, butylamine, hexylamine, dodecylamine, octadecylamine, or benzylamine, or an aromatic primary amine such as aniline or p-methoxyaniline in the presence of a base such as potassium acetate, sodium hydroxide, or potassium hydroxide in a non-reactive polar solvent such as those mentioned in Step (2) of Reaction Scheme I to provide a dithiocarbamate salt VI, see Bogemann et al., infra.

Step (2) is carried out by adding a bis(alpha-haloketone) such as a 4,4,-bis(alpha-haloalkanoyl)diphenyl ether in a polar solvent to the dithiocarbamate salt, followed by treatment [Step (3)]with 0.1 to 10 equivalents of an aqueous acid of pH 6 or less. The bis(alpha-haloketone) in which B is an arylene group can be readily prepared by Friedel-Crafts acylation as outlined in Higgens et al., *J. Polym. Sci.*, (Pt. A-1), 9, 763 (b 1971), and by Longone et al., *J. Polym. Sci.*, (Pt. A.), 3, 3117 (1965). The preparation of a bis(alpha-haloketone), wherein B is an aliphatic group and $R^1$ is hydrogen, is described by V. H. Schubert et al., *J. Prakt. Chem.*, 24, 132–142 (1964). The reaction times, temperatures, solvents, and acids are essentially the same as for Steps (2) and (3) of Reaction Scheme I.

The products of Formulae II and III are readily isolated by conventional methods such as precipitation/filtration, extraction, and chromatography.

Representative compounds of Formula II include:

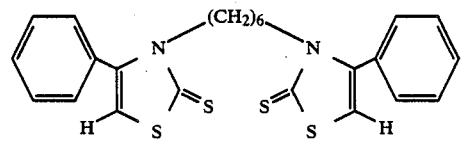

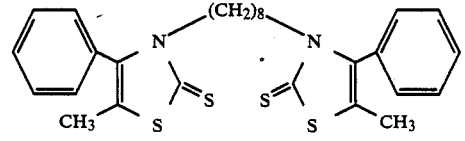

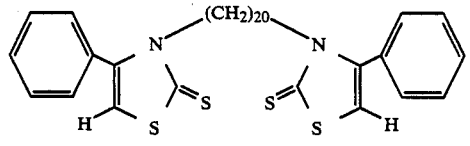

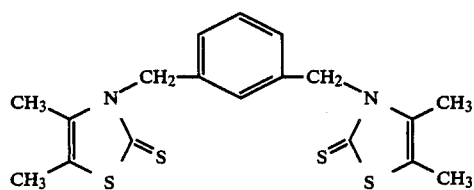
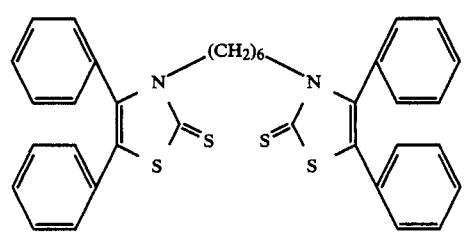
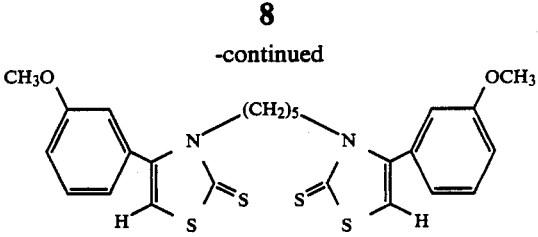
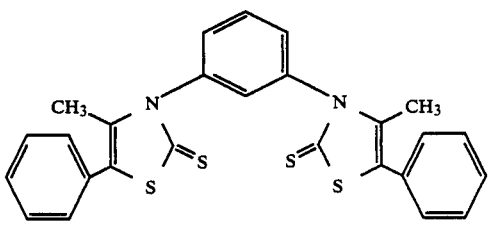
Representative compounds of Formula III include:
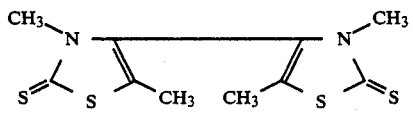
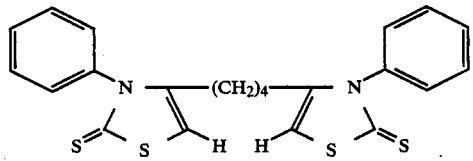
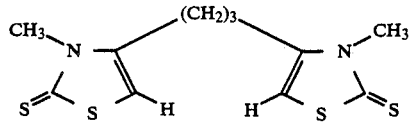
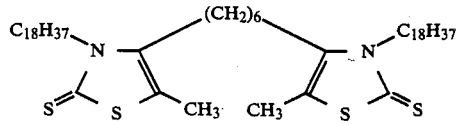
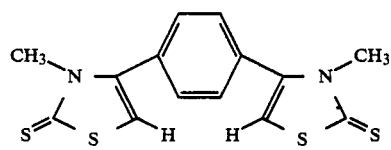
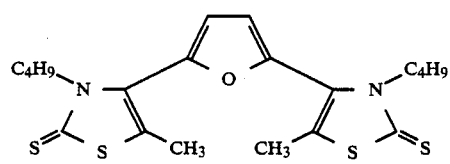

-continued
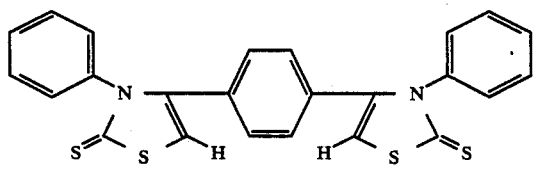
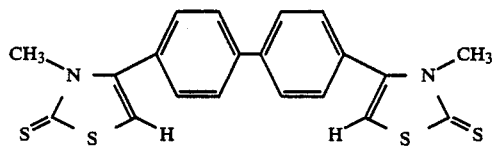
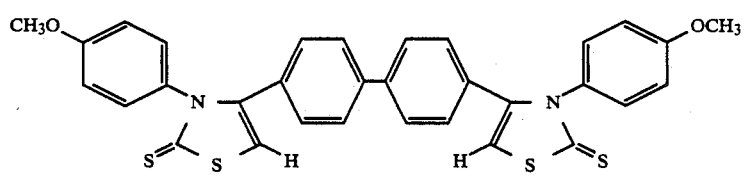
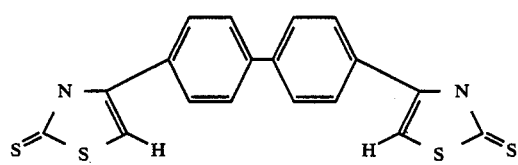
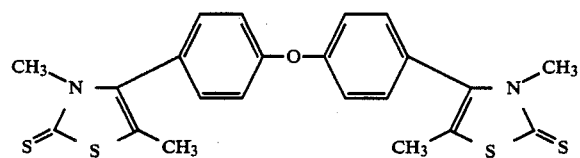
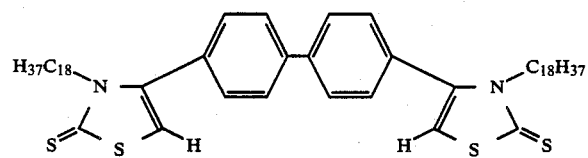
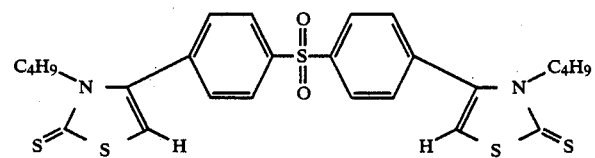
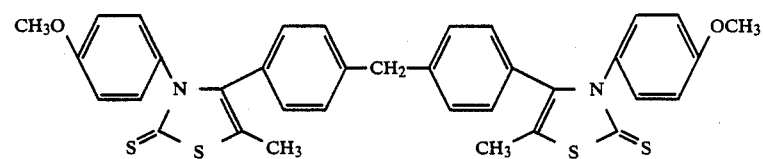
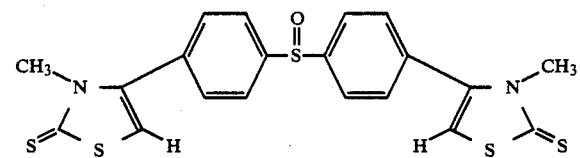

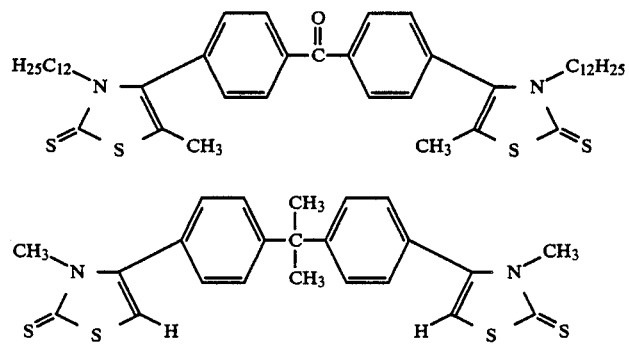

The compounds of the invention are useful as non-migrating components in photosensitive materials. More specifically, they are useful as antifoggants for reducing background imaging in photographic materials, as sensitizers to increase the photosensitivity of silver halide emulsions, and as toners to enhance the black tone of images provided by silver halide emulsions. An effective amount of the bis(thiazolinethiones) can be included in emulsions or with other resinous materials (e.g., in an amount in the range of 0.001 weight percent to 5 weight percent, preferably 0.01 to 0.5 weight percent) or, can be coated out of polar organic solvents by methods known in the art such as roll-coating, dip-coating, bar-coating, knife-coating, etc.

Objects and advantages of this invention are further illustrated by the following examples, but the particular materials and amounts thereof recited in these examples, as well as other conditions and details, should not be construed to unduly limit this invention.

EXAMPLE 1

Preparation of 3,3′-(1,3-propanediyl)bis[4-phenyl-5-methylthiazolin-2-thione], a compound depicted by Formula II:

Potassium acetate (3.92 grams; 0.04 mole), 1,3-propanediamine (1.48 grams; 0.02 mole), and ethanol (50 mL) were charged into a 250-mL round-bottomed flask equipped with a dropping funnel and a magnetic stirring bar. The resulting solution was cooled to 0–5° C. by means of an ice-water bath. A solution of carbon disulfide (3.22 grams; 0.042 mole) dissolved in ethanol (25 mL) was added dropwise over the course of about 20 minutes so that the temperature of the reaction mixture, a white slurry as the addition proceeded, did not exceed 5° C. The mixture was then stirred and warmed to room temperature for another four hours. A solution of alpha-bromopropiophenone (Aldrich; Milwaukee, WI) (8.52 grams, 0.04 mole) dissolved in ethanol (25 mL) was then added over a 10 minute period. By the end of the addition, the reaction mixture was nearly a solution. Even after stirring at room temperature for an additional 48 hours, however, a small quantity of undissolved solid remained. At this point concentrated hydrochloric acid (10 mL) was added, and the mixture was refluxed for one hour. During the reflux period a slightly off-white crystalline solid precipitated. Upon cooling and filtering, 10.12 grams of this solid were obtained. After recrystallization from methylene chloride-acetone, the solid, now off-white needles weighing 5.66 grams (62% yield), melted at 196°–197.5° C. The structure of the compound was corroborated by IR and NMR spectra and by elemental analysis.

The compound can be included in an amount of 0.01 weight percent in a standard silver halide emulsion to increase the sensitivity of a photographic material.

EXAMPLES 2–11

Employing the procedure of EXAMPLE 1, compounds having the structure of Formula II with substituents listed in TABLE I were prepared.

TABLE I

Formula II

| Example | $R_1$ | $R_2$ | A | % Yield | m.p. (°C.) |
|---|---|---|---|---|---|
| 2 | H | $C_6H_5$ | —$(CH_2)_6$— | 97 | 166–167 |
| 3 | H | $C_6H_5$ | —$(CH_2)_2$— | 25 | 251–252 |
| 4 | H | $C_6H_5$ | —$(CH_2)_3$— | 76 | 205–207 |
| 5 | H | $C_6H_5$ | —$CH_2CHCH_2$—<br>\|<br>OH | 43 | 210–210.5 |
| 6 | H | $C_6H_5$ | —$(CH_2)_3O(CH_2)_4$—<br>—$(CH_2)_3O$— | 22 | 133–133.5 |
| 7 | H | $C_6H_5$ | —$(CH_2)_4$— | 13 | 159–161 |
| 8 | H | $4\text{-}CH_3OC_6H_4$ | —$(CH_2)_3$— | 22 | 188–191 |

TABLE I-continued

Formula II

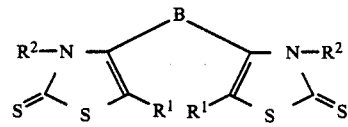

| Example | R₁ | R₂ | A | % Yield | m.p. (°C.) |
|---|---|---|---|---|---|
| 9 | H | C₆H₅ | —(CH₂)₃N(CH₂)₃— <br> \| <br> CH₃ | 22 | 147–149 |
| 10 | CH₃ | CH₃ | —(CH₂)₃— | 48 | 202.5–205 |
| 11 | CH₃ | CH₃ | —CH₂—C₆H₄—CH₂— | 30 | 238.5–240 |
| 12 | C₆H₅ | C₆H₅ | —(CH₂)₃— | 28 | 260–261.5 |
| 13 | H | 3-nitro-C₆H₄— | —(CH₂)₃— | 80 | 256–257 |

EXAMPLE 14

Preparation of 4,4′-bis(3-methylthiazolin-2-thion-4-yl)biphenyl, a compound depicted by Formula III:

Carbon disulfide (1.52 grams; 0.02 mole) dissolved in ethanol (3.4 mL) was added to potassium acetate (1.98 grams; 0.02 mole) and methylamine (40% aqueous) (1.74 grams; 0.02 mole) dissolved in N,N-dimethylformamide (50 mL). The resulting solution was stirred for 2 hours before addition of 4,4′-bis(bromoacetyl)biphenyl (prepared by the method of J. Higgens, et al., *J. Polym. Sci. A*-1, 9, 763 (1971)) (3.96 grams; 0.01 mole) dissolved in N,N-dimethylformamide (50 mL). After stirring for 36 hours at room temperature, concentrated HCl(5mL) was added, and the mixture was warmed to 80° C. for 3 hours. The reaction mixture was poured into water (500 mL), and the white crystalline product that precipitated was filtered. Drying the solid yielded 7.8 grams of product which melted at 254°–255° C. after recrystallization from acetic acid. The structure of the compound was corroborated by IR and NMR spectra and by elemental analysis.

EXAMPLES 15–16

Employing the procedure of EXAMPLE 13, compounds having the structure of Formula III with substituents listed in TABLE II were prepared.

TABLE II

Formula III

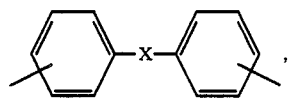

| Example | R₁ | R₂ | B | % Yield | m.p. (°C.) |
|---|---|---|---|---|---|
| 15 | H | CH₃ | p-(C₆H₄)₂O | 65 | 214–216 |
| 16 | H | C₁₈H₃₇ | p-(C₆H₄)₂ | 67 | 129.5–130 |

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A compound having the formula

III

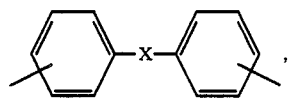

wherein

R¹ is hydrogen, a lower alkyl group having 1 to 4 carbon atoms, or an aryl group having 5 to 12 ring atoms, R² is hydrogen, an alkyl group of 1 to 20 carbon atoms, or an aryl group of 5 to 12 ring atoms, B is a carbon to carbon single bond, a branched or straight chain alkylene group having 1 to 20 carbon atoms that can be interrupted by one or more nonadjacent oxygen or sulfur atoms, an arylene group having 5 to 12 ring atoms, or a arene group of 6 to 20 atoms, or $$\text{(phenyl)—X—(phenyl)},$$

wherein X is a branched or straight chain alkylene group of 1 to 4 R4

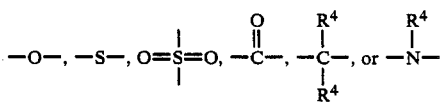

wherein R⁴ is independently H or a lower alkyl group.

2. The compound according to formula III of claim 1 wherein B is a single carbon to carbon bond, or a trimethylene, tetramethylene, hexamethylene, or octamethylene group.

3. The compound according to claim 1 wherein B is para-phenylene; para, para'-biphenylene; para, para'-oxydiphenylene; para, para'-thiodiphenylene; para, para'-methylenediphenylene;

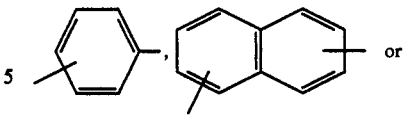, 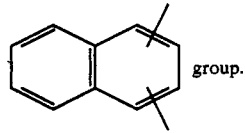 group.

4. The compound according to claim 1 wherein $R^1$ is hydrogen, methyl, or phenyl.

5. The compound according to claim 1 wherein $R^2$ is methyl, phenyl, p-methoxyphenyl, or m-nitrophenyl.

* * * * *

UNITED STATES PATENT AND TRADEMARK OFFICE
CERTIFICATE OF CORRECTION

PATENT NO. : 4,946,962
DATED : August 7, 1990
INVENTOR(S) : Steven M. Heilmann et al.

It is certified that error appears in the above-identified patent and that said Letters Patent is hereby corrected as shown below:

On the title page, under "Inventors", "Steven J. Heilmann" should read -- Steven M. Heilmann --.

Col. 14, line 61, kindly delete "R4" and insert therefor -- carbon atoms, --.

Signed and Sealed this

Nineteenth Day of May, 1992

Attest:

DOUGLAS B. COMER

*Attesting Officer*    Acting Commissioner of Patents and Trademarks